United States Patent [19]
Schmid

[11] Patent Number: 5,125,405
[45] Date of Patent: Jun. 30, 1992

[54] BIOMEDICAL ELECTRODE FOR USE ON HUMAN OR VETERINARY PATIENTS

[76] Inventor: Walter Schmid, Fuchsweg 9, 7914 Pfaffenhofen, Fed. Rep. of Germany

[21] Appl. No.: 411,375

[22] Filed: Sep. 25, 1989

[30] Foreign Application Priority Data

Feb. 27, 1989 [DE] Fed. Rep. of Germany ......... 396071

[51] Int. Cl.⁵ .............................................. A61B 5/04
[52] U.S. Cl. .................................. 128/640; 128/639; 128/798
[58] Field of Search ............... 128/639, 640, 641, 644, 128/802; 604/20

[56] References Cited

U.S. PATENT DOCUMENTS

| | | |
|---|---|---|
| 3,072,973 | 4/1959 | Barnette . |
| 3,170,013 | 12/1960 | Ploetz . |
| 3,690,211 | 5/1972 | Brody . |
| 4,066,078 | 1/1978 | Berg . |
| 4,126,126 | 11/1978 | Bare et al. ............... 128/639 |
| 4,213,463 | 7/1980 | Osenkarski ............. 128/639 |
| 4,233,987 | 11/1980 | Feingold .................. 128/639 |
| 4,270,543 | 6/1981 | Tabuchi et al. . |
| 4,272,471 | 6/1981 | Walker . |
| 4,273,135 | 6/1981 | Larimore et al. . |
| 4,317,278 | 3/1982 | Carmon et al. . |
| 4,368,167 | 1/1983 | Berchielli . |
| 4,406,827 | 9/1983 | Carim ..................... 128/639 |
| 4,554,294 | 11/1985 | Engel . |
| 4,554,924 | 11/1985 | Engel . |
| 4,570,637 | 2/1986 | Gomes et al. .......... 128/639 |
| 4,583,548 | 4/1986 | Schmid ................... 128/639 |
| 4,629,595 | 12/1986 | Ito . |
| 4,640,289 | 2/1987 | Craighead . |
| 4,692,273 | 9/1987 | Lawrence . |
| 4,722,761 | 2/1988 | Cartmell et al. . |
| 4,750,976 | 6/1988 | Hupe et al. .............. 204/15 |
| 4,798,642 | 1/1989 | Craighead ............. 128/639 |
| 4,852,571 | 8/1989 | Gadsby et al. . |
| 4,860,754 | 8/1989 | Sharik et al. .......... 128/802 |
| 4,979,517 | 12/1990 | Grossman et al. ..... 128/802 |

FOREIGN PATENT DOCUMENTS

| | | |
|---|---|---|
| 0085327 | 8/1983 | European Pat. Off. . |
| 0096330 | 12/1983 | European Pat. Off. . |
| 2459627 | 6/1975 | Fed. Rep. of Germany ...... 128/639 |
| 57-27623 | 2/1982 | Japan . |

Primary Examiner—Stephen C. Pellegrino
Assistant Examiner—Steven J. Shumaker
Attorney, Agent, or Firm—Venable, Baetjer, Howard & Civiletti

[57] ABSTRACT

A body electrode comprising one or more galvanically active sensors, a first layer capable of adhering to the skin on the body contact side and a non-adhesive covering second layer on the side of said sensors opposite the body contact side. The first layer comprises an electrically conducting adherent, elastic hydrophilic material. The body electrode is characterized by the fact that the first layer and the second layer have been produced by mold casting. The chief advantage of such electrodes is the fact that they may be produced by casting in a simple and cost-effective manner, thus avoiding stamping processess.

28 Claims, 3 Drawing Sheets

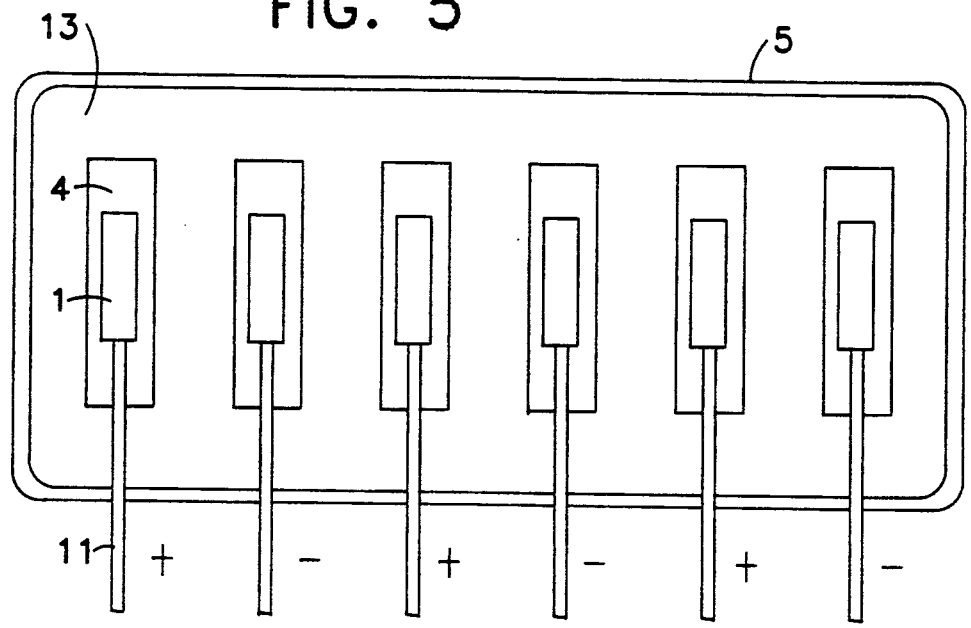
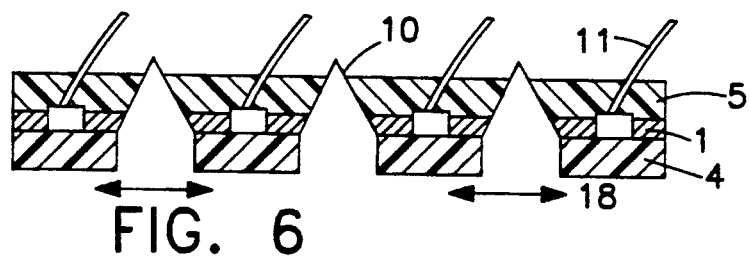
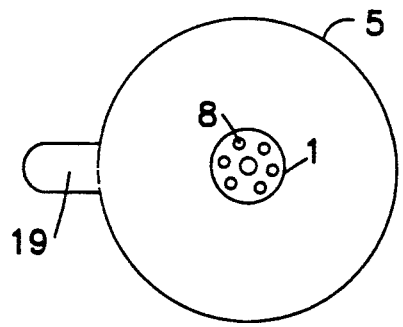
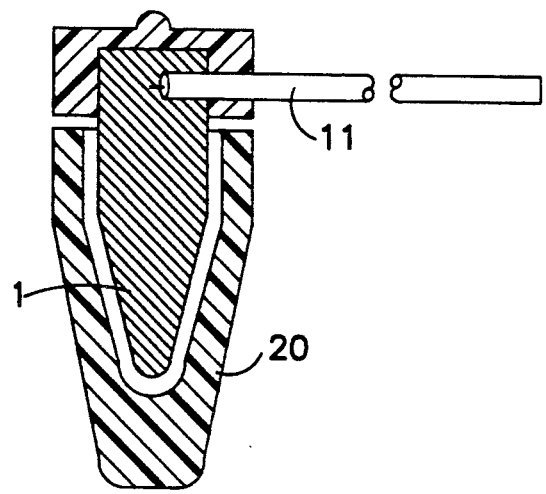

BIOMEDICAL ELECTRODE FOR USE ON HUMAN OR VETERINARY PATIENTS

The invention relates to a body electrode or biomedical electrode.

Such electrodes are known (see, for example, U.S. Pat. Nos. 4,554,924 and 4,066,078, as well as DE-AS 28 14 061). They are fastened to the skin of the patient to be examined or treated and serve the purpose of transmitting electrical signals from the body to a recording instrument, or in the opposite direction, signals from a device to the body. They are used, for example, to record electrocardiograms, as ground electrodes in operations, or to mitigate pain through transmission of electrical pulses.

These electrodes essentially comprise one or more generally plate-shaped galvanically active sensors which have a place of attachment for an electric conductor leading to a recording device or transmitting electric pulses from a device into the body. The sensor is connected on its body contact side to a first layer capable of adhering to the skin and consisting of an electrically conductive, adherent, elastic hydrophilic material or combinations of materials. This layer serves the purpose of ensuring firm adhesion of the body electrode to the skin while smoothing out unevennesses of the body to make certain of transmission of electric signals from the body by way of the sensor to a display unit or of a signal generated in an instrument by way of the sensor into the body.

The known electrodes are manufactured by stamping in the desired size and shape, from a wide continuous strip, the adherent layer which comes in contact with the skin, a sensor then being applied to the preform obtained and then, if the first layer coming in contact with the skin is larger in area than the sensor plate, a covering and supporting second layer also produced by stamping is aligned with and applied to the first layer. Considerable problems arise in stamping out the adhesive first layer which contacts the skin, because it is difficult to remove the stamped adhesive parts from the stamping tool.

Hence, the task was set for the invention to develop a body electrode which avoids the stamping processes in the manufacture of the electrode. This task is accomplished by the body electrode described and claimed herein.

The body electrode according to the present invention comprises an electrically conductive, elastic and hydrophilic first layer capable of adhering to the skin, one or more conventional plate-like sensors, and a non-conducting and non-adhesive electric covering second layer covering the side of the electrode facing away from the body of the first layer. The layers are manufactured by mold casting, so that the problems described above as arising in the stamping of these layers, in particular the adhesive first layer, no longer occur.

It is advisable for the ratio of the area of the first layer adhering to the skin to the area of the plate-like sensor or sensors to be higher than one, and in particular, two to three. That is, it is advisable to use the smallest possible sensor in relation to the first layer. This arrangement is particularly expedient if, in accordance with another preferred embodiment of the invention, both the first layer adhering to the skin and the second covering layer are transparent, so that observation of the skin contact surface of the patient to be treated is possible. In this manner, it can be determined if skin irritations occur, especially when the electrode is applied for a prolonged period of time.

The body electrode of the present invention is preferably designed so as to be ring-shaped or square, but it may also be produced in any other shapes.

The first layer capable of adhering to the skin expediently comprises a conducting natural and/or synthetic material, in particular a polymer material, which for example may be an elastomeric polymer or a collagen. In addition, this layer may comprise a non-conductive natural or synthetic material which then contains an electrolyte to produce conductivity. It may also be expedient for the first layer adhering to the skin to contain a tackifying agent, a plasticizer, and/or a hygroscopic agent, so that the adhesive properties, the elastic properties, and the hygroscopicity may thus be customized.

The covering second layer preferably comprises a natural or synthetic non-conductive material which expediently is also a polymer, preference being given to elastomers (elastomeric polymers) or collagens.

The first layer adhering to the skin and the covering second layer may comprise the same material, it naturally being necessary to render the layer adhering to the skin conductive, by addition of an electrolyte, as well as adherent. The adhesiveness can be achieved by addition of a tackifying agent or, if cross-linkable polymers are employed to produce the two layers, by less strongly cross-linking the first layer coming in contact with the skin than the covering second layer, if the polymer is sufficiently adhesive in the less strongly cross-linked state.

According to another preferred embodiment of the invention, the body electrode may have an intermediate transparent layer which is provided with, for example, symbols, inscriptions, or graphic images, if the layer adhering to the skin and/or the covering layer are transparent. In this manner, it is possible to identify the electrode from the viewpoint of origin.

All known sensors are suitable for the body electrode of the present invention, for example, those described in DE-OS 24 59 627, U.S. Pat, Nos. 4,554,924 and 4,066,078, DE-AS 28 14 061, and DE-OS 29 35 238. A plate-like sensor equipped with a push-button type wiring point for an electric lead has been found to be especially suitable, as has a sensor which is coated with a conducting, galvanically active material such as a silver/silver chloride layer. The sensors may preferably also comprise polymers representing a reversible redox system. Such materials are known in the art.

Generally speaking, although a plate-like sensor which is mostly round is employed in the body electrode of the invention, it is also possible to employ as a sensor the conductor or conductors of the electric lead or leads by means of which signals are transmitted to a recording device. In this particularly cost-effective embodiment, an electric lead with a silver conductor, e.g., one coated with a silver chloride layer, is preferably employed.

In addition, microspheres coated with zinc or silver, for example, may be used as galvanically active sensors, such as the materials marketed under the brand name Metalite TM. A suitable number of these microspheres are positioned between the first layer coming in contact with the skin and the covering second layer and are connected to an electric lead leading to a recording device. The sensors and/or the electric leads may also comprise layers which are applied to sheeting, as for example, by screen printing.

If a plate-like sensor is used in the electrode of the invention, the plate element of the sensor preferably has recesses, in particular holes, which ensure better anchoring of the first layer coming in contact with the skin and/or the covering second layer.

It is also possible to transmit electric signals received from the body to a recording device by a wireless method. The electrode may be outfitted for this purpose with an integrated circuit characterized by low power consumption and energized by a power source such as a round cell. If the electrode of the invention is to be applied to the thorax, for example, it is advisable for the electrode to be elastic in the longitudinal direction. In this use, an embodiment of a body electrode is provided which comprises several electrode units connected by sheeting folded in an accordion-like arrangement allowing extension of the electrode in the longitudinal direction, as for example during inhalation and the accompanying enlargement of the thorax.

The invention is illustrated in detail in the accompanying FIGS. 1-8, identical parts being identified by the same reference numbers in these figures.

FIG. 5 is a top view of an electrode designed as a stimulation electrode.

FIG. 6 is a vertical section through an electrode of the invention which is extensible in the longitudinal direction.

FIG. 7 is a top view of a ring-shaped electrode with a sensor, the plate element of which is provided with holes.

FIG. 8 is a vertical section through an electrode of the invention which is useful for EEG recording.

Figure 1:
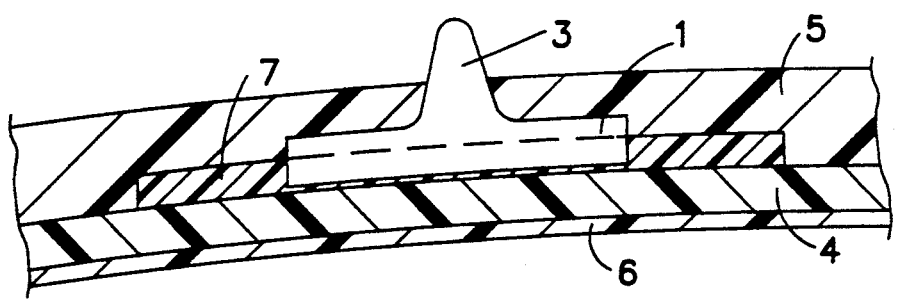
FIG. 1 shows a vertical section through an embodiment of the electrode of the invention with a sensor.

The embodiment of the body electrode shown in FIG. 1 comprises a plate-like round sensor 1 with a wiring point for an electric lead leading to a recording device. The sensor may comprise one of those described in the references cited above. On its side facing the body, the sensor is provided with a first layer capable of adhering to the skin 4, which may comprise any known natural or synthetic material which is elastic, mild to the skin, non-toxic and hydrophilic, and which adheres to the skin. A prerequisite for this material is that it must be castable in any form. The material in question preferably comprises a synthetic, preferably elastomeric, polymer or a polymer mixture and/or a collagen. This material is either conductive or rendered conductive by addition of an electrolyte. Preferably synthetic organic polymers or polymer mixtures which either are intrinsically conductive or are rendered conductive by addition of an electrolyte are used to produce the first layer 4. These polymers must be castable in the form of a solution, a melt, or a prepolymer of suitably low viscosity. An abundance of polymers meeting these requirements are available. Suitable as conducting polymers, for example, are the polymers described in U.S. Pat. No. 4,066,078 of 2-acryl-amido-2-methylpropane sulfonic acid, its salts, copolymers of the acid named, copolymers of the salts of the acid, and mixtures thereof mixed with water, alcohols and mixtures thereof; the polymers described in DE-OS 29 35 238 with at least 5 mole percent monomer units and containing a sale of a carboxylic acid; and conductive polymer compounds which consist of a hydrophilic cross-linked polymer, and a hydrophilic non-cross-linked polymer, which are described in EP 85 237.

Among the polymers which are not conductive as such and are rendered conductive by addition of an electrolyte include, among others, polyvinyl alcohols, polyvinyl acetates, polyvinyl propionates, and polyvinyl ethers such as are described, for example, in *Adhesion* 5/81, pages 208-213, as well as polyacrylates and polymethacrylates such as those described in DE-OS 31 36 366, U.S. Pat. No. 4,554,924, and DE-AS 28 14 061. The unsaturated acrylate resin types marketed by BASF under the brand name Laromer TM have been found to be especially suitable, most preferably the resin marketed under the brand name Laromer EA-8812 TM. To increase or to control adhesiveness, these polymers may additionally contain one or more tackifying agents such as the glycidyl ether acrylates and their derivates known to be suitable for this purpose. In addition, they may contain plasticizers (softeners) and/or hygroscopic agents, i.e., polyols such as diols and triols, for example, hexane triols, polyethylene glycol, etc. It is expedient that the polymers also contain added bacteriostatics and odor absorbing agents such as eucalyptol.

As has already been noted, the polymers employed to produce the first layer coming in contact with the skin 4 are cast in the castable state in a mold, either in the form of a solution, a melt, or a prepolymer hardenable by cross-linking. The latter embodiment is preferred. The hardening is preferably accomplished by irradiation with ultraviolet light and/or heat by the use of known photoinitiators and/or hardening accelerators. Examples of suitable compounds include per compounds such as peroxides and/or ketone hardening accelerators, for example, 2-hydroxy-2-methyl-1-phenyl-propan-1-one, which is an efficient photoinitiator for acrylated epoxides, acrylated polyurethanes, acrylated polyethers, and acrylated unsaturated polyesters or mixtures thereof. The adhesion, conductivity and elastic properties of the first layer coming in contact with the skin 4 can be customized by varying the type and amount of the conducting polymer employed, either ones naturally conductive or ones rendered conductive by addition of an electrolyte and of any tackifying agent, plasticizer, and/or hygroscopic agent introduced, and also of the degree of cross-linking or hardening. Preferably alkali halides such as potassium chloride are used as electrolytes to render non-conducting polymers conductive for production of the layer 4.

The material for the covering or second layer 5 may be any known natural and/or synthetic hydrophilic material which is also castable in the form of a solution, a melt, or a cross-linkable or hardenable prepolymer and which bonds with the first layer 4 on solidification. The material for the cover layer must of course not be conductive and must also contain no additives imparting conductivity. As with the first layer, the second layer may be transparent. The many known materials meeting the specified requirements include, among others, polymers, especially elastomeric polymers, gelatins, especially ossein with a gelatin strength of 60 to 160 Bloom and a cast gelatin Shore hardness of 40 to 90 Shore, as well as in particular the polyacrylates used to produce the first layer 4. These polyacrylates must be cross-linked or hardened to the extent that they are no longer adhesive for the covering second layer 5. Hence, in accordance with the invention, preference is to be given to using the same polyacrylate prepolymers employed to produce the first layer to produce the second covering layer 5, but which are more extensively cross-linked or hardened so that they are no longer adhesive. An especially strong bonding of the polymers of the first layer 4 and the polymers of the second layer 5 is thereby achieved.

In the embodiment shown in FIG. 1, an intermediate layer 7 provided with symbols is positioned between the first layer coming in contact with the skin 4 and the covering second layer 5. As with the second layer and the first layer, the intermediate layer 7 comprises a transparent material so that symbols applied to this layer 7 can be recognized when the electrode is examined. This layer also comprises a castable natural or synthetic material. It is possible to employ the same materials used to produce layers 4 and 5. However, the layer 7 must not be conductive. In addition, symbols may be applied to the upper side of the covering second layer 5 facing away from the body, for example, by imprinting, pasting on, or painting. However, it is advisable for any embossed symbols to be applied to the upper side of the covering second layer 5 which have been obtained by casting the covering layer in a mold with corresponding indentations. In this case the body electrode is not produced, as described in greater detail later, by casting the first layer coming in contact with the skin, applying the sensor, and then casting the covering second layer. Instead, the process is carried out in the reverse order for this particular embodiment.

The first layer adhering to the skin is provided with a detachable protective layer 6, which may consist of any material that may be separated from the first layer adhering to the skin, a material which is preferably water-repellent and/or is provided with a releasing coating such as a silicone coating. It is especially advantageous for the protective coating 6 to consist of the mold in which the body electrode is produced by casting of the layers 4 and 5, and if applicable, the layer 7. That is, the body electrode is not removed from the mold after casting but rather is marketed as a unit with this casting mold, the casting mold being detached when the electrode is used. The covering second layer 5 preferably has a tab (not shown) to make removal from the mold easier.

Figure 2:
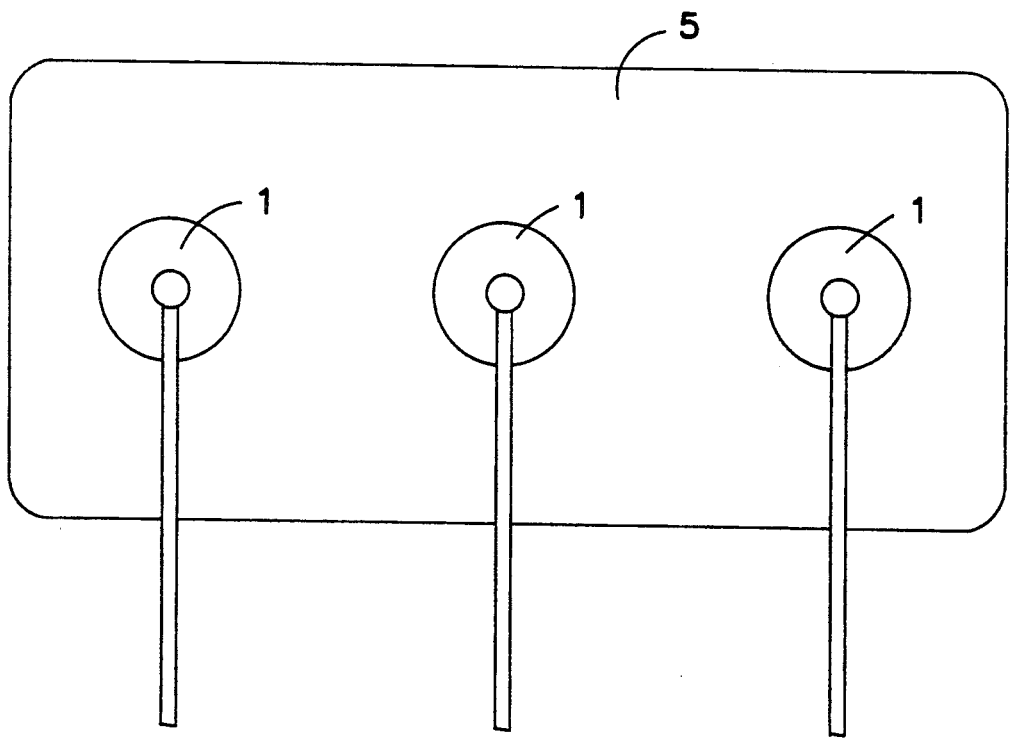
FIG. 2 is a top view of a body electrode which is provided with three sensors.

The body electrode shown in FIG. 2 is rectangular in shape and contains three circular sensors. In this case, the electrical conductors whereby these sensors may be connected to a display unit are not connected to the sensor at a push-button type wiring point as in the case of the embodiment shown in FIG. 1. Instead, they are fastened to the sensors without a push-button type connection device and are embedded in the horizontal plane of the body electrode in the covering second layer 5, from the lateral edge of which they project. These electrical conductors 11 may consist of conventional connecting cables, but they preferably consist of carbon fibers and/or conducting plastics.

Figure 3:
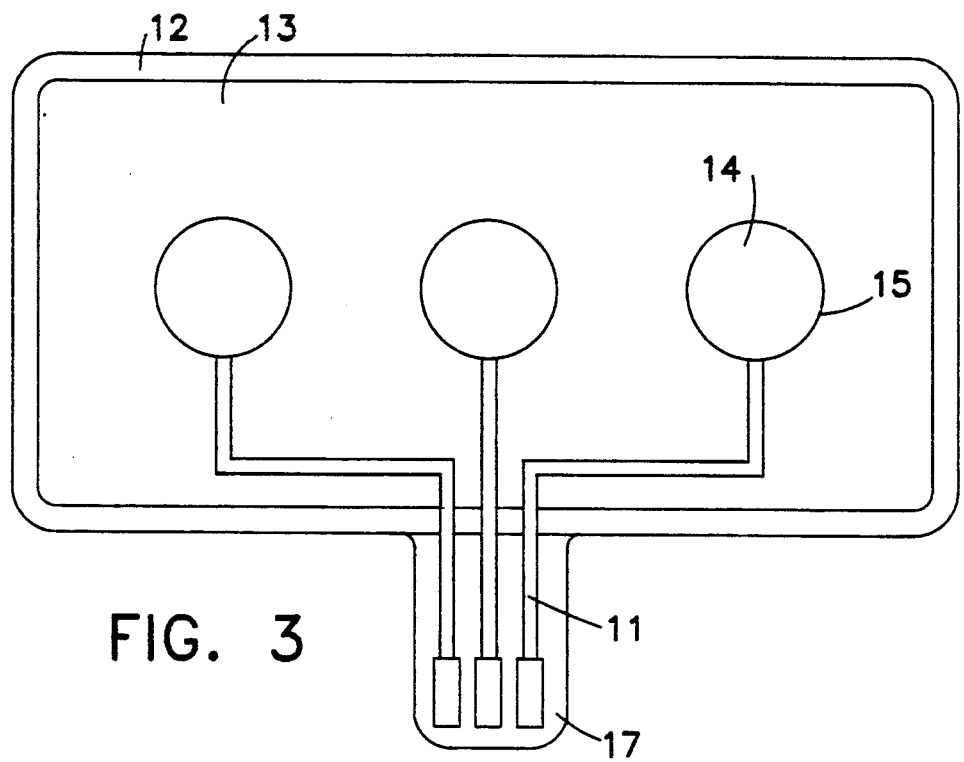
FIG. 3 is a top view of another embodiment of such an electrode.

FIG. 3 also shows a rectangular body electrode with three sensors, the electric leads 11 connected to these sensors ending in a connection tab 17 from which connection may be made to a recording device. In this embodiment, round recesses provided in the cast covering layer 12 are filled with a conductive adhesive material such as is used to produce the first layer adhering to the skin. Sheeting 13 coated in areas 15 with a galvanically active layer is applied to this structure. The sheeting 13 has connection leads 11 which are also applied by coating. The sheeting 13 may be coated with the galvanically active layer or with the electric leads, for example, in a screen-printing process.

Figure 4:
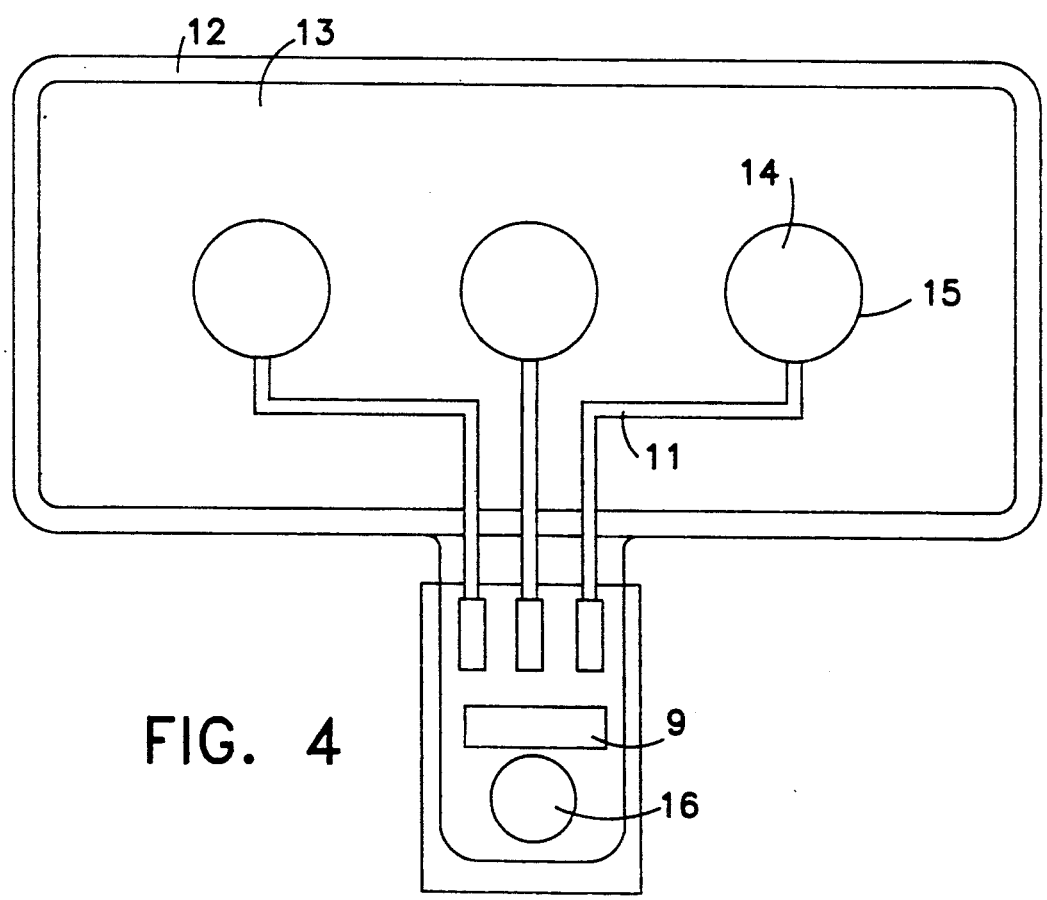
FIG. 4 is a top view of an embodiment of such an electrode outfitted with a transmitter.

FIG. 4 shows an embodiment similar to that shown in FIG. 3, but in this case the electric leads 11 are connected to a transmitter 9 powered by a round cell 16. This transmitter forwards signals transmitted from the body by wireless means to a recording device.

FIG. 5 shows an electrode which may be used as a stimulation electrode with polarity selectable as required. This electrode comprises a cast covering second layer 5 with recesses in which the material of the first layer adhering to the skin 4 is cast, galvanically active sensors 1 with the corresponding electric leads which are in contact with the first layer 4 being applied to the sheeting 13 corresponding to the embodiment shown in FIG. 3. An electrode such as this is used to transmit signals generated in a device, for example, to mitigate pain.

FIG. 6 shows an electrode which comprises several individual electrodes and which is extensible in the longitudinal direction 18. It comprises four individual electrodes which are connected on the sides of their covering second layer 5 by sheeting folded in the shape of an accordion. The sheeting used consists preferably of a plastic, especially an elastomeric plastic, that can be bent without forming cracks. The four sensors of this electrode may be connected by leads 11 to a display unit. In this embodiment, and also the embodiment shown in FIG. 1, the sensor may comprise a strip of a galvanically active metal or of a plastic which is coated with a galvanically active metal. This strip projects in bent form through the center of the covering second layer 5 and may be connected by an electric lead to a display unit.

FIG. 7 shows a top view of a body electrode essentially corresponding to the one shown in FIG. 1. The plate of the circular electrode is provided with holes 8 to ensure better anchoring both in the first layer coming in contact with the skin (not shown) and in the covering second layer 5. When the electrode plate is applied to the freshly cast first layer adhering to the skin and when the covering second layer 5 is cast, the holes in the materials involved are penetrated, with the result that good anchoring is achieved. The electrode has a tab 19 on its covering layer 5 side to facilitate removal from the casting mold.

The thickness of the first layer coming in contact with the skin 4 in the embodiments of flat body electrodes described above ranges preferably from 800 $\mu$m to 2,500 $\mu$m, and with particular preference from 1,000 $\mu$m to 2,000 $\mu$m, while the thickness of the covering second layer 5 preferably ranges from 500 $\mu$m to 2,500 $\mu$m, and especially from 1,000 $\mu$m to 2,000 $\mu$m. Circular electrodes of the embodiments illustrated in FIGS. 1 and 7 preferably have diameters ranging from 20 mm to 60 mm. The thickness of the electrode plate of the plate-like electrodes used in these electrodes ranges preferably from 50 $\mu$m to 1,500 $\mu$m, and especially from 80 $\mu$m to 1,000 $\mu$m.

An additional embodiment of an electrode of the present invention comprises a contact cap such as that shown in FIG. 8 which is to be placed preferably on the head and used for EEG recording. This contact cap comprises a tapering contact body 20 which is open at the wider end and which is produced by casting. This contact body 20 consists of a non-adhesive conducting material in which a sensor 1 with an electric connecting lead 11 is introduced and held stationary by a clamping force of the contact body 20. This contact cap is fastened on the parts of the body for which measurements are to be made, preferably the head, by means of adhesive tape or the like. To protect the contact body 20, it may be marketed in the mold in which it was cast, devised as a protective layer.

The body electrodes of the invention are produced, avoiding stamping processes, by casting processes described in detail in a copending application entitled "Process for Manufacturing a Body Electrode," Ser. No. 412,296 filed as follows:

This casting essentially comprises casting the first layer adhering to the skin in a casting mold, applying the sensor 1 to this layer, casting any intermediate layer bearing symbols, and then casting the covering second layer 5. The process may also be carried out in the reverse order, in particular to produce body electrodes as illustrated in FIGS. 4 and 5, by first casting the covering second layer, if applicable, with corresponding recesses to receive the first layer, casting the first layer coming in contact with the skin in the recesses, and then connecting the sensors to the layer coming in contact with the skin.

What is claimed is:

1. A biomedical electrode comprising one or more galvanically active sensors, a first layer having adhesive properties on the body contact side of said sensors capable of adhering to the skin and comprising an electrically conductive, adherent, elastic hydrophilic material, and a second layer covering the sensors and the first layer, on the side opposite the body contact side and comprising an elastic, non-adherent material, both said first layer and second layer having been molded by casting whereby said first and second layers are bonded together by cross-linking or by adhesion as a result of said casting.

2. The body electrode of claim 1, wherein the first layer and the second layer are transparent.

3. The body electrode of claim 1, wherein the ratio of the area of the first layer to the area of the sensors is greater than 1.

4. The body electrode of claim 3, wherein the ratio is from about 2 to about 3.

5. The body electrode of claim 1, wherein the body electrode is ring-shaped or square.

6. The body electrode of claim 5, wherein the protective coating comprises a casting mold of the electrode.

7. The body electrode of claim 1, wherein the first layer comprises a conducting synthetic material.

8. The body electrode of claim 7, wherein the material is a polymer.

9. The body electrode of claim 7, wherein the first layer further comprises one of the group of a tackifying agent, a plasticizer, and a hygroscopic agent.

10. The body electrode of claim 1, wherein the first layer comprises a non-conducting material which contains an electrolyte.

11. The body electrode of claim 10, wherein the material is a polymer.

12. The body electrode of claim 10, wherein the first layer further comprises one of the group of a tackifying agent, a plasticizer, and a hygroscopic agent.

13. The body electrode of claim 1, wherein the second layer comprises a non-conducting natural or synthetic material.

14. The body electrode of claim 13, wherein the material is a polymer.

15. The body electrode of claim 1, wherein the first layer and the second layer comprise the same cross-linkable non-conducting polymers, the polymer of the second layer being more strongly cross-linked.

16. The body electrode of claim 1, wherein the first layer has a detachable protective coating.

17. The body electrode of claim 1, wherein the body electrode further comprises a third intermediate layer, the first layer and the second layer are transparent, and the third layer is transparent, provided with symbols and inserted between the first and second layers.

18. The body electrode of claim 1, wherein the sensor has a wiring point for an electric lead.

19. The body electrode of claim 18, wherein the electrode lead contains a conductor or conductors and the conductor or conductors is the sensor.

20. The body electrode of claim 19, wherein the electrode further comprises a sheeting layer and the sensors consist of layers of galvanically active materials applied on said sheeting.

21. The body electrode of claim 20, wherein said application is by screen printing.

22. The body electrode of claim 1, wherein the sensors are plate-like and have recesses in them.

23. The body electrode of claim 22, wherein the body electrode is extensible in the longitudinal direction.

24. The body electrode of claim 1, wherein the electrode further comprises a sheeting layer and the sensors consist of layers of galvanically active materials applied on said sheeting.

25. The body electrode of claim 24, wherein said application is by screen printing.

26. The body electrode of claim 1, wherein the sensor is connected to a transmitter.

27. The body electrode of claim 1, wherein the body electrode contains several sensors.

28. The body electrode of claim 1, wherein the ratio of the area of the first layer to the area of the second layer is less than 1.

* * * * *